United States Patent
Hsieh

(10) Patent No.: US 10,837,942 B2
(45) Date of Patent: *Nov. 17, 2020

(54) METHOD AND APPARATUS TO CHARACTERIZE PRESSURIZED LIQUID SAMPLE

(71) Applicant: Wyatt Technology Corporation, Goleta, CA (US)

(72) Inventor: Hung-Te Hsieh, Santa Barbara, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/451,949

(22) Filed: Jun. 25, 2019

(65) Prior Publication Data
US 2019/0317045 A1 Oct. 17, 2019

Related U.S. Application Data

(63) Continuation of application No. 15/407,157, filed on Jan. 16, 2017, now Pat. No. 10,330,638.

(51) Int. Cl.
| | |
|---|---|
| *G01N 27/447* | (2006.01) |
| *G01N 21/53* | (2006.01) |
| *G01N 33/15* | (2006.01) |
| *G01N 15/00* | (2006.01) |
| *G01N 21/33* | (2006.01) |
| *G01N 21/64* | (2006.01) |
| *G01N 21/41* | (2006.01) |
| *G01N 21/05* | (2006.01) |
| *G01N 21/47* | (2006.01) |

(52) U.S. Cl.
CPC ....... *G01N 27/44721* (2013.01); *G01N 15/00* (2013.01); *G01N 21/53* (2013.01); *G01N 33/15* (2013.01); *G01N 21/33* (2013.01); *G01N 21/4133* (2013.01); *G01N 21/64* (2013.01); *G01N 2015/0038* (2013.01); *G01N 2015/0053* (2013.01); *G01N 2015/03* (2013.01); *G01N 2021/054* (2013.01); *G01N 2021/479* (2013.01)

(58) Field of Classification Search
CPC .. G01N 27/44721; G01N 21/33; G01N 21/53; G01N 21/64; G01N 33/15; G01N 15/00; G01N 2021/479; G01N 2015/0038; G01N 2015/0053; G01N 2015/03; G01N 2021/054; G01N 21/4133
USPC .................. 356/432–448, 335–343
See application file for complete search history.

(56) References Cited

U.S. PATENT DOCUMENTS

| | | | | |
|---|---|---|---|---|
| 5,738,133 | A * | 4/1998 | Seki ................. | G01N 30/32 137/115.26 |
| 10,330,638 | B2 * | 6/2019 | Hsieh ............... | G01N 33/15 |

* cited by examiner

*Primary Examiner* — Tri T Ton
(74) *Attorney, Agent, or Firm* — Leonard T. Guzman

(57) ABSTRACT

A method and apparatus for measuring the physical properties of a drug formulation suspended in a pressurized liquid propellant and a system to enable such measurements is disclosed. Drug formulations suspended in pressurized liquid propellant used in Pressurized Metered Dose Inhalers (pMDIs) are propelled in their native liquid state into an analytical instrument with a measurement cell capable of withstanding the pressure required to retain the sample in liquid form by employing a device to rapidly release the contents of the pMDI canister into the measurement instrument wherein the sample's electrophoretic mobility and size may be determined by MP-PALS or other techniques. A series of valves permits the maintenance of the high pressure in the system. Once the measurements are made, the pressurized liquid is allowed to pass to waste or another analytical instrument by opening an exit valve.

13 Claims, 4 Drawing Sheets

METHOD AND APPARATUS TO CHARACTERIZE PRESSURIZED LIQUID SAMPLE

PRIORITY

This application is a continuation of U.S. patent application Ser. No. 15/407,157, filed Jan. 16, 2017.

RELATED APPLICATIONS AND PATENTS

The following patents relate to the measurement of the electrophoretic mobility of particles and are hereby incorporated by reference:

U.S. Pat. No. 8,411,638 B2, H.-T. Hsieh and S. P. Trainoff, "Apparatus to measure particle mobility in solution with scattered and unscattered light," issued May 14, 2013.

U.S. Pat. No. 8,525,991 B2, H.-T. Hsieh and S. P. Trainoff, "Method to measure particle mobility in solution with scattered and unscattered light," issued Sep. 3, 2013.

U.S. Pat. No. 9,335,250 B2, S. P. Trainoff, "Bubble suppressing system for optical measurement cells," issued May 10, 2016.

BACKGROUND

Chronic obstructive pulmonary disease (COPD), including asthma, chronic bronchitis and emphysema, affects an estimated 330 million people worldwide. COPD has been and is projected to continue to be the third leading cause of death in the next two decades.

Management of COPDs necessarily involves periodic and precise administration and dosing of therapeutic agents delivered into respiratory airways. These agents are generally administered by aerosol formulations through the mouth or nose. One device for dispensing aerosol drug formulations is called a pressurized metered-dose inhaler (pMDI). A drug formulation is suspended in liquefied gas known as a propellant. This suspension is stored at a pressure which maintains the propellant in a liquid state within a sealed container capable of withstanding this pressure. The container is connected to a dose metering valve that, when activated, dispenses a predetermined amount of aerosolized suspension into the respiratory airway. Active drug ingredients commonly used in pMDIs include corticosteroids and bronchodilators, for example $\beta_2$ adrenergic receptor antagonists and muscarinic receptor antagonists. The pMDIs can contain one or more active ingredients.

The liquefied pMDI propellant, being gaseous at atmospheric pressure, serves two major purposes: it is the vehicle that suspends and carries the therapeutic components and it aerosolizes and propels the drugs into respiratory airways upon gasification following actuation of the pMDI metering valve. The typical vapor pressure inside a pMDI ranges from 400 to 700 kPa (4 to 7 atm), depending on the propellant mixture, ambient temperature and the specific formulation. Ozone-layer-damaging chlorofluorocarbons (CFCs) were first used as pMDI propellants but have been gradually phased out over the years in favor of hydrofluoroalkanes (HFAs). However, since HFAs are greenhouse gases, the search for the next generation of pMDI propellants is ongoing.

There are many factors that can affect the proper dosage and delivery of the drug formulations contained within a pMDI, from malfunctioning metering valves to adherence of aerosol drugs to the inner surfaces of the container to manufacturing defects. Also the stability of the therapeutic suspensions in pMDI propellants has important consequences for drug efficacy and safety.

Challenges to proper dosing and dispensing of medications from pMDIs must be addressed in an efficient manner to provide the proper treatment to COPD patients. Further, it is required that the prescribed dose of aerosol medication delivered to the patient consistently meets the specifications required by regulating agencies such as the U.S. Food and Drug administration as well as the prescribing medical professional. Quality assurance methods for the measurement of the proper delivered dose have been developed, see for example U.S. Pat. No. 5,261,538, "Aerosol testing method," issued Nov. 16, 1993. In order to discourage adherence of the drug formulation to the walls of pMDI container special coatings have been developed specific to individual drug formulations as discussed in U.S. Pat. No. 6,253,762, "Metered dose inhaler for fluticasone propionate," Issued Jul. 3, 2001. With the goal to provide quality assurance in pMDIs and to aid in the search for propellants to be used in these devices, the present invention provides a method to test the stability of the therapeutic suspensions within a pMDI.

DETAILED DESCRIPTION OF THE INVENTION

Figure 1:
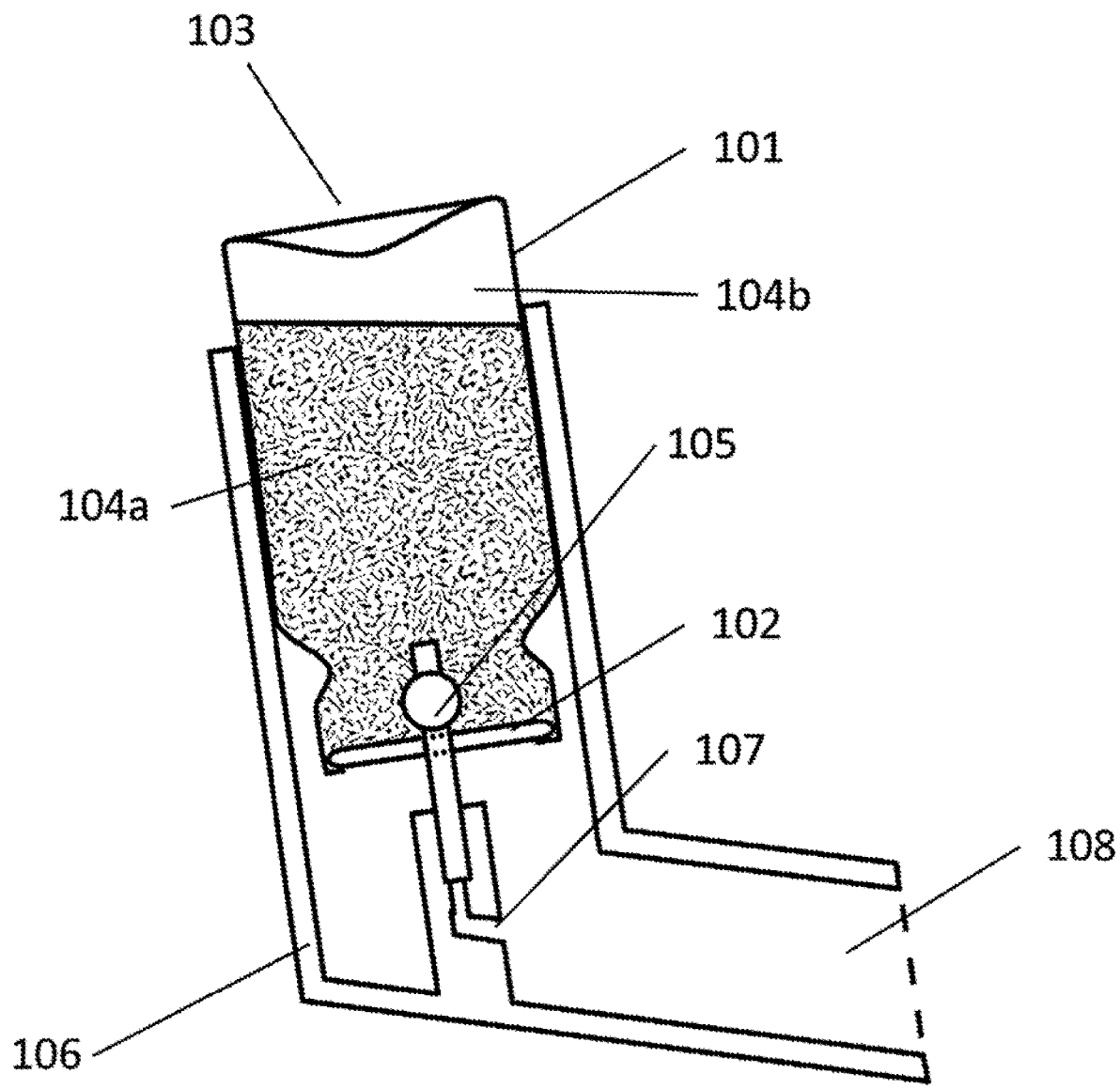
FIG. 1 shows a basic representation of the elements of an example pressurized metered-dose inhaler (pMDI).

A pressurized Metered-Dose Inhaler (pMDI) generally consists of the key elements, shown in FIG. 1. A can 101 and cap 102, generally made of aluminum, comprise an enclosure that contains the drug formulation and propellant in liquid 104a and gaseous 104b phases. As the formulation is dispensed from the canister, a small amount of the contents in liquid phase 104a will evaporate into gaseous phase 104b in order to keep the closed system in equilibrium, and this will maintain the pressure within the canister until all of the liquid contents are expended. This sealed canister 103 must be capable of containing the pressurized liquid at ranges typically from about 400 to 700 kPa. Passing through the cap of the canister is a drug metering valve 105 that, when actuated, permits a precise amount of drug suspending fluid to escape the canister. Actuation of the valve is generally performed by pushing the canister 103, with the actuation valve facing downwards, into the body of an actuator 106. When the liquid formulation is released from the canister through an actuator nozzle 107, the escaping liquid extracts heat from the environment and evaporates quickly, aerosolizing the suspended drug in the process. The escaping aerosol is then directed by the actuator nozzle toward the respiratory airway of the patient, generally through a mouthpiece 108.

As discussed previously there are many potential problems associated with the system which could have deleterious effects for the COPD patient. Naturally, the stability of the therapeutic suspensions in the pMDI propellants has important consequences for the drug efficacy and safety. It is possible to determine the colloidal stability by measuring the electrophoretic mobility (zeta potential) of the suspended particles over time as well as monitoring their size. A higher mobility correlates with better colloidal stability as a result of long range electrostatic repulsion. However, measurements of the electrophoretic mobility of propellant suspended drug formulations have not heretofore been possible due to the fact that the pMDI propellants quickly boil away under standard atmospheric pressure and temperature. While the mobility and size of the drug formulation itself can be characterized if dissolved or suspended in various solvents that exist in liquid state at STP to infer colloidal stability, a definitive stability assessment must be carried out with the actual propellant as the suspension medium, which cannot be performed at STP as the propellants do not exist in the liquid state at these pressures and temperatures.

The present invention enables a means to measure the electrophoretic mobility and particle size of the drug formulation suspended within the liquefied pMDI propellants in which they are stored. This method not only permits very accurate measurement of electrophoretic mobility as well as size analysis, but enables quality assurance measurements of current inventory pMDI canisters and allows a given lot of canisters to be tested over time for mobility and size stability, permitting, thereby a high quality evaluation of the suitability and longevity of a given propellant with a given drug formulation suspension.

A key component required for the present invention is a measurement cell capable of operating at pressures required to retain the pMDI propellant in a liquid state. Further, the entire system must be able to sustain this high pressure for the duration of the measurement. The Möbiuζ® electrophoretic mobility detector manufactured by Wyatt Technology Corporation (Goleta, Calif.), for example, employs a measurement cell designed to operate at high pressures permitting a pressurized liquid sample to be contained therein. This high pressure tolerance has permitted the instrument to be combined with a bubble mitigation system as discussed in U.S. Pat. No. 9,335,250 B2. However, this high pressure tolerant measurement cell has not heretofore been used to measure the electrophoretic mobility of fluids that must be maintained at high pressure in order to remain a liquid state. Indeed, U.S. Pat. No. 9,335,250 describes a system specifically designed such that the measurement cell is never exposed to fluid from the pressure source. Not until the inventive method disclosed herein has the high pressure capability of the Möbiuζ cell, or the cells of other high pressure capable instruments, been utilized to actually make measurements where the samples themselves are held at high pressure in order to maintain their liquid state.

Figure 2:
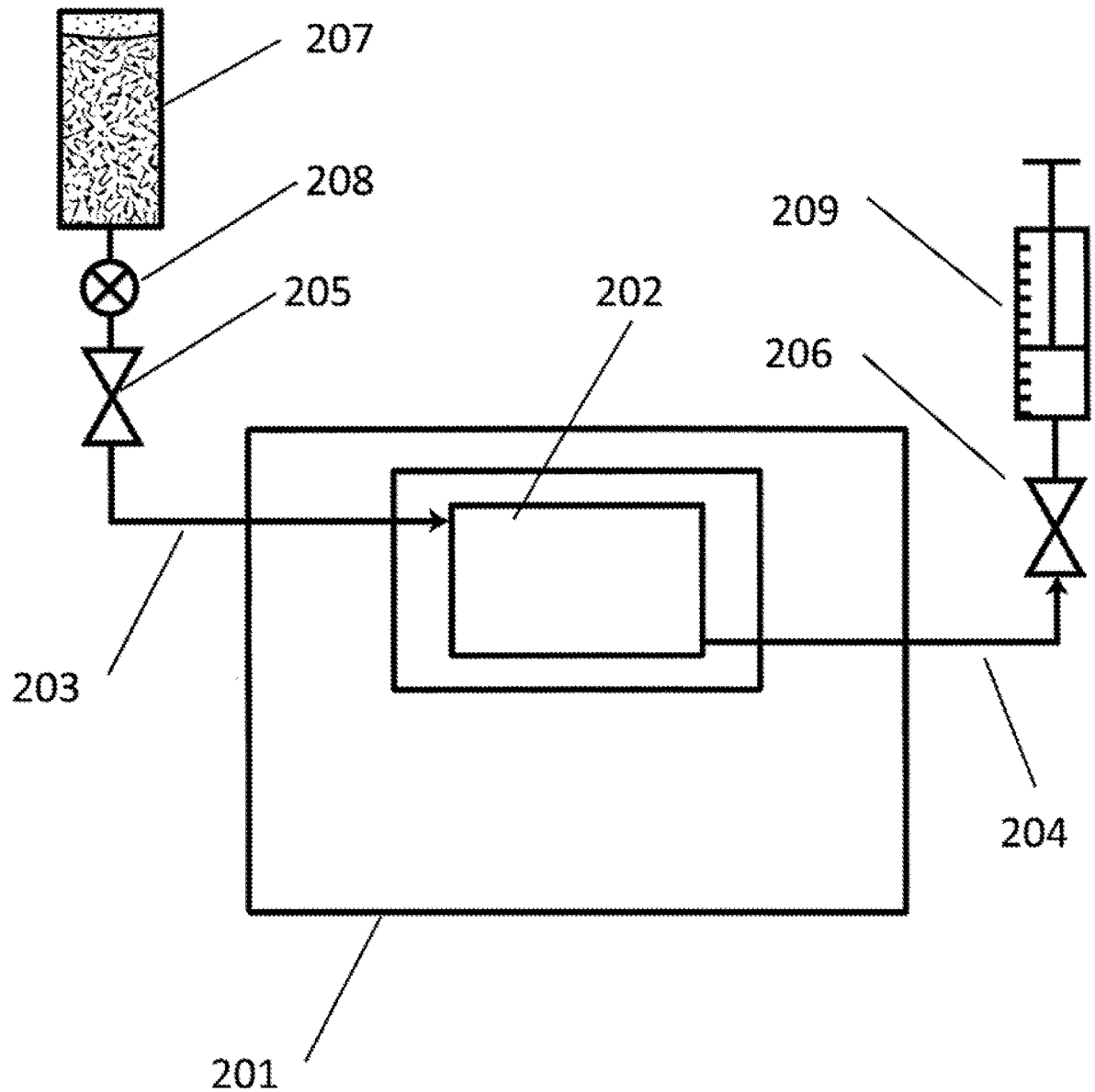
FIG. 2 illustrates a system to measure various physical properties of the pressurized liquid sample contained in a pMDI.

One embodiment of the invention shown in FIG. 2 comprises a sealed, air-tight sample measurement system 201 including a measurement cell 202 as well as other components necessary for analytical measurements of the sample contained within the system. For example, the cell of an electrophoretic mobility detector will contain electrodes, and, if the detector 201 is a massively parallel phase analysis light scattering detector, such as that described by Hsieh and Trainoff in U.S. Pat. No. 8,411,638 B2, it will also contain a laser beam, associated optics, and other elements necessary for measuring sample parameters such as electrophoretic mobility and particle size. Samples can be guided into and out of the measurement system by way of the inlet tubing 203 and outlet tubing 204. The lengths of inlet and outlet tubing are gated by inlet and outlet valves 205 and 206 respectively that can be open or closed. To introduce sample from the pMDI vessel 207 for measurement, the inlet tubing 203 is connected to the pMDI vessel 207 by some form of a rapid release adapter or mechanism 208, which bypasses the generally built-in metering valve, while both the inlet and outlet valves are closed. The inlet valve 204 is then opened and the propellant from the pressurized vessel 207 fills the open volume of the measurement system 201, including the measurement cell 202 and any interconnecting tubing, filters, pressure regulators, etc., with the liquefied suspension of interest. The vapor pressure within the pMDI vessel 207 ensures that the suspension remains liquefied for characterization.

It is important that the pMDI 207 be oriented such that, when connected to the inlet tubing, it is the liquid phase present in the canister that is propelled into the system. For example, as the less dense gaseous propellant will rise to the top of the interior of the canister, it is preferable that the canister is accessed on the end opposite to region containing gaseous propellant to avoid filling the instrument with gas rather than liquid. Alternately, gas traps could be set within the flow path to encourage the flow of any gaseous sample out of the measurement cell 202. Gas bubbles trapped within the measurement cell could contribute to errors in the measurement.

It is a good idea to apply Boyle's law and confirm that the atmosphere initially present in the flow path, including the inlet and outlet tubing and sample chamber, under the propellant's vapor pressure can be compressed out of the measurement cell 202 instead of interfering with the subsequent measurements. In order to ensure this, it should be verified that the liquefied pMDI suspension volume is larger than the sample chamber volume, and that the outlet tubing 204 volume is large enough to accommodate the propellant-compressed atmosphere. Alternatively, to facilitate even easier introduction of sample into the measurement cell 202, one can first purge the sample space. With the inlet valve 205 closed and the outlet valve 206 open, a purging device such as a syringe 209 is used to evacuate the atmosphere contained within the cell 202 and dead volume between the inlet valve 205 and the outlet valve 206. The outlet valve 206 is then closed and the inlet valve 205 is opened to permit the liquefied suspension from the pMDI canister 207 to fill the chamber. Since the atmospheric pressure within the chamber has been greatly reduced by purging prior to filling the system, the liquefied pMDI suspension readily fills up the sample chamber. With each embodiment of the inventive method the vapor pressure within the pMDI canister 207 conveniently keeps the suspension liquefied during measurements. The chamber contents can be discharged after measurements by first closing valve the inlet valve 205 and then opening the outlet valve 206. Subsequent samples may be introduced in the same manner.

Figure 3:
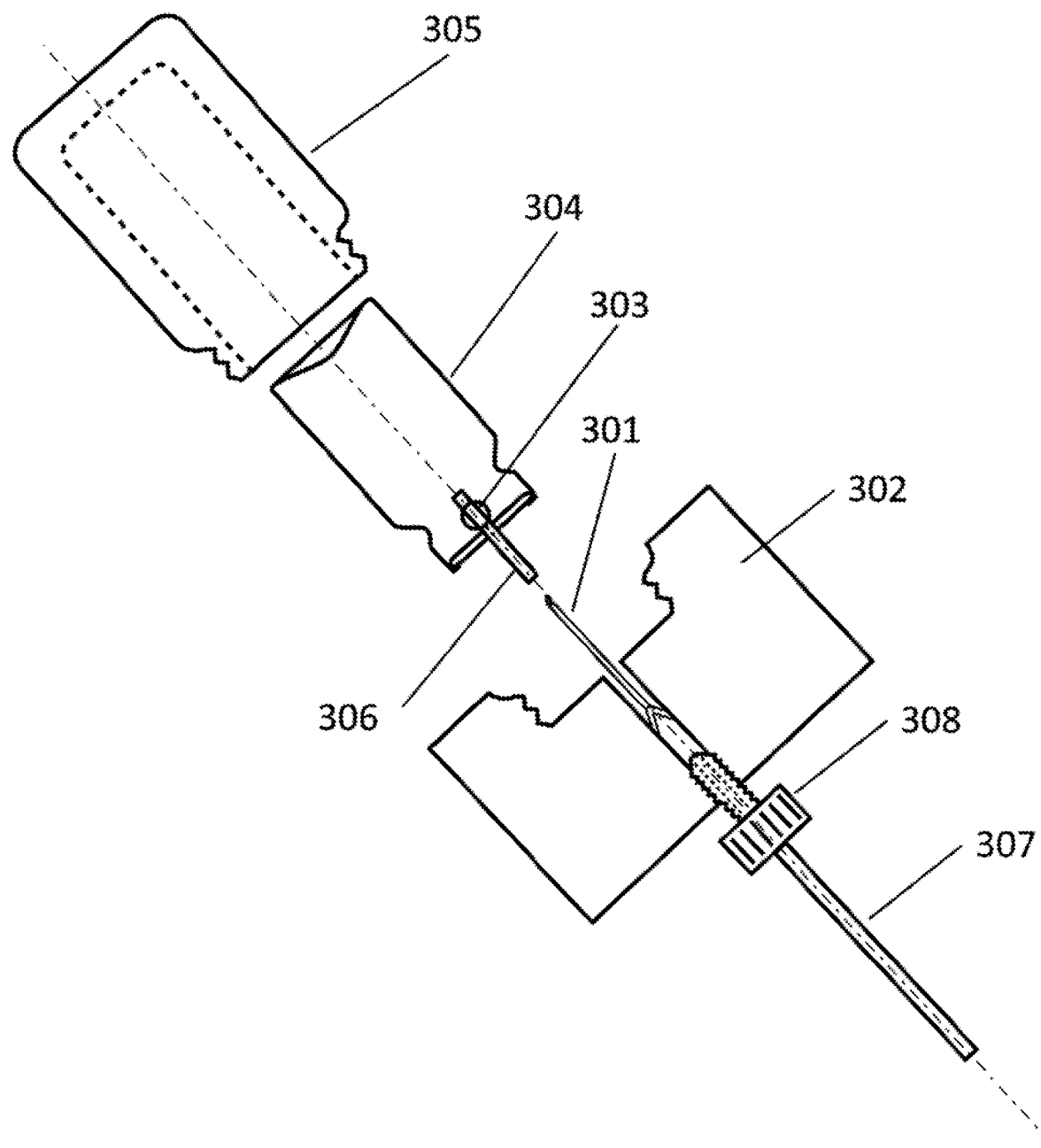
FIG. 3 shows one potential embodiment of a rapid release adapter used to permit the injection of the pressurized liquid sample into a measurement device.

Various means for the rapid release of the contents of a pMDI are known to those in the art and the rapid release adapter 208 can take any form known in the art to perform a contained release of the contents of the canister, from specialized or proprietary release mechanisms to a simple contained and controlled puncture of the vessel 207 itself, so long as the liquid sample is directed into the inlet tubing 203 and not allowed to escape into the environment, ensuring thereby that the sample remains in pressurized, liquid form. One simple embodiment of a rapid release adapter is shown in FIG. 3. This simplified system employs a syringe needle 301, such as a hypodermic, within a fluid release assembly 302 to pierce the metering valve 303 of the pMDI canister 304. The canister 304 can be placed within a threaded pressure resistant receiving element 305, and the needle 301 can be directed into the metering valve outlet 306. With the receiving element 305 holding the canister 304, and the end of the needle 301 directed into the metering valve outlet 306, the receiving element can be threaded into the corresponding fluid release assembly 302, creating a seal and driving the needle to puncture the metering valve 303. As the assembly is now a closed system, the only means for the pressurized sample to escape is through the inlet to the system tubing 307 connected to the fluid release assembly 302 by a fitting 308. This rapid release adapter configuration is only one of many possible means by which the pressurized sample within the pMDI canister may be released, and different pMDI manufacturers will likely require different means to bypass the metering valve to allow direct flow of the pressurized sample from the canister.

While the critical elements to the system have been discussed above, there are many variations which may add both utility and versatility to the method and system described. For example a pressure relief valve may be installed in the instrument or along the flow path, with the pressure required to activate the relief mechanism selected so as to permit only as much pressure within the system as the measurement cell is designed to withstand and that the instrument can reliably accept before leaking. Utilizing a pressure relief valve acts as a failsafe mechanism in the event that an over-pressurized or incompatible pMDI is connected to a system incapable of accepting such pressures without damage.

Another element which may be added to the system is one or more gas traps placed in-line with the sample path. The extra volume of a gas trap would help to ameliorate passage of any gaseous materials into the measurement cell, which could cause errors in measurement if gas bubbles manage to get trapped therein. In addition, if a pMDI canister is incorrectly oriented when the contents are released with the rapid release adapter and gaseous propellant precedes a flow of the liquid propellant; it may be possible to capture the gaseous contaminants prior flow entry into the measurement cell. A gas trap located downstream from the measurement cell will ensure that gaseous sample evaporating as the fluid fills the measurement system will be collected downstream from the measurement cell, rather than potentially being trapped therein. Of course the volume of any gas trap must be selected to ensure that fluid along the path will not evaporate into the traps in sufficient volume such that the measurement cell itself is not filled with liquid sample.

Another variation on the method and system described above would be the addition of another two way valve within the flow of the exit tubing or the replacement of a two-way exit valve with a three-valve, with the exit from the measurement cell connected to one port, a syringe for purging the system, as discussed above, connected to another port, and the last port connected to a waste line, which can either vent the liquid sample to the atmosphere, be connected to any of a number of gaseous sample capturing devices, or be directed to another analysis system, such as that described in U.S. Pat. No. 5,261,538.

It also may prove advantageous to add a flow restriction element in line with the inlet tubing, such as a length of narrow bore capillary or a mechanical flow restrictor, which allows the pressurization rate of the measurement cell to be controlled by restricting the flow rate of the liquefied sample into the measurement cell.

A variation on the system illustrated in the drawings uses a measurement cell with fluid passing there through taking a vertical path where passage of the sample into the cell is from the bottom and exiting from the top of the cell. This would encourage any gaseous sample passing along the path to exit the cell prior to it being filled with pressurized liquid sample. The cell might also be constructed such that it is tapered at the outlet region to encourage any trapped bubbles to flow upwards to the exit port rather than possibly getting trapped in any corners of the cell.

Other variations can include replacing the on-off valves discussed thus far with other elements to control flow into and/or out of the instrument. For example, an exit valve, that can be in an open or shut position, could be replaced with a flow restrictor element which is selected to limit flow out of the measurement instrument to such a rate that adequate time is permitted to perform a measurement on the liquid sample and retain the sample in a liquid state within the cell prior to the sample flowing or evaporating through the flow restrictor. One embodiment of the invention would require no valves at all, flow into the system would begin with the actuation of the rapid release adapter, causing liquid to flow directly into the measurement cell, and a flow restrictor at the outlet of the cell permitting the sample to escape therethrough at a slow enough rate that by the time the sample within the cell has been allowed to vaporize, a measurement has been made. Then an operator need only remove the spent pMDI canister and replace it with another for analysis.

Another possible configuration of an apparatus for performing the inventive method would be the inclusion of an additional pressurization system, such as the Atlas™ pressurization system (Wyatt Technology Corporation, Goleta, Calif.) to a valve connected to the outlet tubing from the system. External pressure applied from an independent system could help to mitigate problems associated with bubbles located within the cell and could aid in maintaining pressure necessary to keep the sample in a liquid state. An adapted version of a system such as the Atlas could be used to deliver the sample itself rather than utilizing a separate rapid release adapter.

Figure 4:
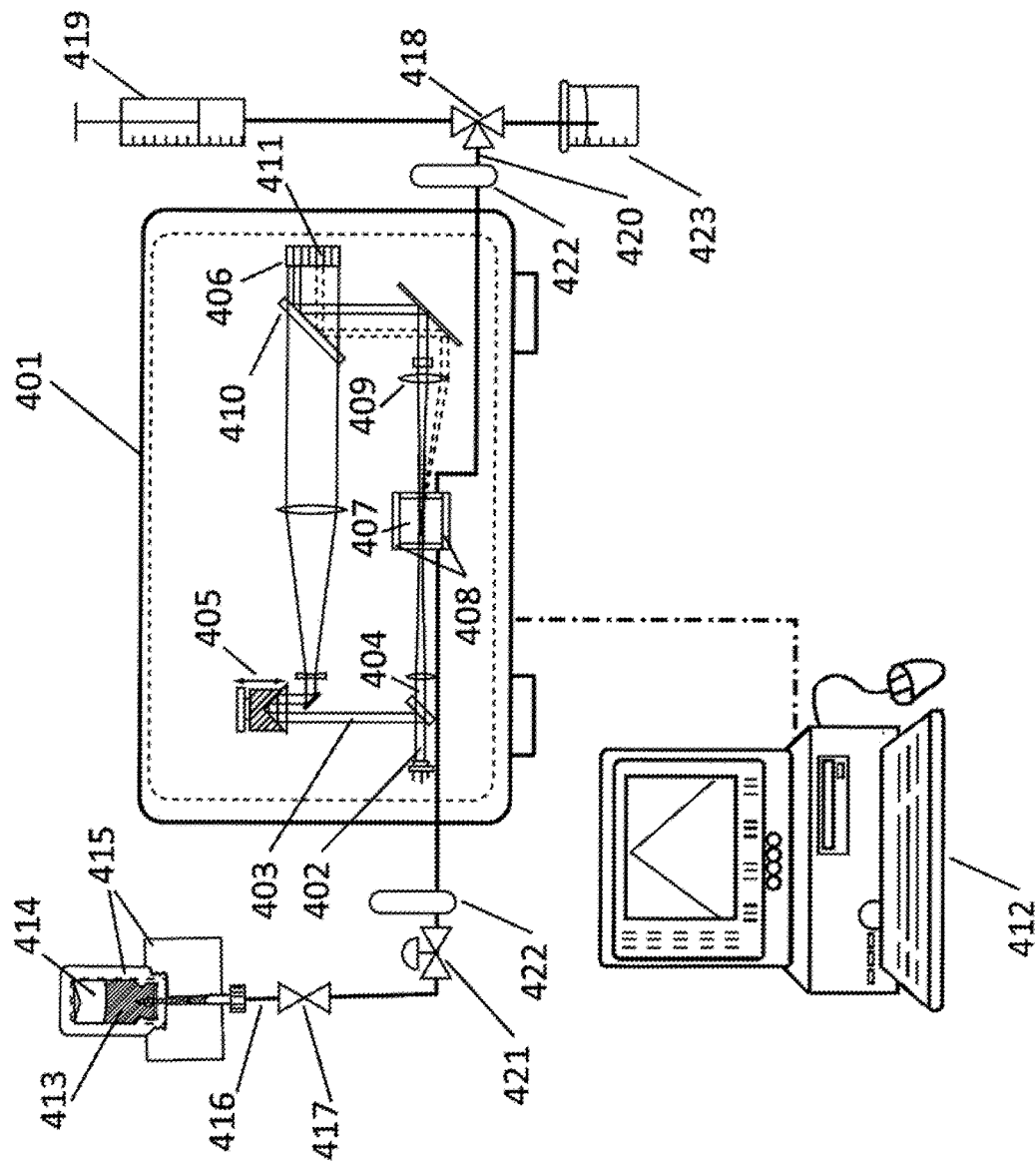
FIG. 4 illustrates an example of the inventive method and system combined with an MP-PALS instrument to perform a measurement of the electrophoretic mobility of a pressurized liquid sample from a pMDI canister.

Merely as means to illustrate the utility of the present invention, consider a non-limiting preferred embodiment wherein the inventive method described herein is employed to make a measurement of electrophoretic mobility using MP-PALS, an innovative implementation of the Phase Analysis Light Scattering technique to measure electrophoretic mobility. As illustrated in FIG. 4, the MP-PALS instrument 401 generally utilizes a coherent beam of laser light 402 split to produce two beams, a reference beam 403 and a sample beam 404. The reference beam is directed to a modulator 405 that impresses upon it a time varying phase modulation. This beam is then expanded and shaped so that it fully illuminates a detector array 406. The sample beam is focused into and passes through a measurement cell 407 containing a liquid sample. Electrodes 408 within the cell apply a time varying electric field to the illuminated sample. The transmitted sample beam, along with a portion of the light scattered by the sample, which now contains information about the motion of the molecules, are collimated by a lens 409. This sample beam is combined with the reference beam by a beam splitter 410 to form an interference speckle pattern on the detector array 406. The array is chosen so that each element covers one or more coherence areas of the speckle pattern and covers a narrow range of scattering angles determined by the focal length of the collimating lens. Since the reference beam is phase modulated, each detector element records a time varying signal with a frequency set by the phase modulator. The electronic signal from each detector element is amplified and filtered by a band pass filter around this frequency. One element on the array, the forward monitor 411, detects interference of the unscattered sample beam and the reference beam. The forward monitor measures the exact phase modulation that was impressed upon the reference beam. This signal is then used to demodulate the signals corresponding to the different scattering angles. The phase difference between the forward monitor and each detector determines the accumulated optical phase, and thereby, the mobility of the sample. The most important benefit conferred by this measurement technique is that each detector element provides an independent, simultaneous measurement. Since the precision of the mobility determination improves with the number of detectors used, an array with a large number of elements is preferred. By averaging a number of elements the time required to achieve a specified precision decreases inversely as the number of elements, enabling the measurement of very small particles. In addition, the reduced measurement time associated with MP-PALS decreases damage to fragile biological samples while minimizing electrochemical degradation of the electrodes 408. The collected data may be stored and analyzed on a computer 412.

In this example using of inventive method with the MP-PALS system described above, the sample to be analyzed 413 contained within the pMDI capsule 414 is released by means of a rapid release adapter assembly 415 into the inlet tubing 416. Inlet valve 417 is closed, prohibiting flow from the capsule into the system. The three-way exit valve 418 is opened to allow fluid access between the flow path within the instrument 401 and the syringe 419. The flow path downstream from the inlet valve is evacuated by withdrawing the syringe. Exit valve 418 is then closed, sealing the exit tubing 420. Inlet valve 417 is then opened, permitting flow of the liquid sample into the system. The pressure regulating valve 421 restricts the rate at which the system can be filled with the liquid sample 414. Gas traps 422 in-line with the flow path trap any gas entering the system and further permitting the cell 407 to fill with liquid at a controlled rate and discouraging the capture of bubbles within the cell itself. Once the cell is filled with the liquid sample, the sample is analyzed by the MP-PALS method described above. When a measurement is complete, the inlet valve 417 may be closed, and the exit valve 418 is switched to a configuration allowing fluid communication between the flow path downstream of the inlet valve and an outlet to waste 423 or to another instrument for further analysis. Alternatively the inlet valve may be left in an open position when the outlet valve is opened, permitting the remaining fluid within the pMDI canister 414 to pass through the system to waste. At this time, the canister may be removed from the rapid release adapter 415 and the system is ready to analyze another sample in the same manner.

While this disclosure has concerned itself primarily with the measurement of pressurized liquid suspensions contained within pMDI canisters, nothing in this specification should be considered limiting its application to pMDIs alone. Indeed any pressurized liquid may be analyzed using this method so long as the pressure required to retain the sample in a liquid state is within the tolerance of the measurement cell and related system. Additionally, while measurement of size and electrophoretic mobility have been primarily discussed within the current specification, any measurement system wherein the sample measurement cell and containing instrument can withstand the pressures required to keep the sample in a liquid state can benefit from the inventive method disclosed herein, including multiangle light scattering (MALS) and dynamic light scattering (DLS) measurements as well as UV absorption, fluorescence, and differential refractive index measurements.

As disclosed above and discussed throughout this specification, the utility of this invention has wide ranging benefits for the analysis of drugs used to treat COPT and other respiratory ailments. With this system, for the first time, for example, the electrophoretic mobility of inventory stock of off the shelf pMDIs can be tested without elaborate means to mimic the in situ characteristics of drug formulations by suspending or dissolving them in solvents which exist in a liquid state at STP. Further, the efficacy and longevity of new propellants can be tested as well as possible interactions they, or the suspended active ingredients contained within the propellant, may have with the canister walls themselves. Further the efficacy of a number of coatings placed upon the interior of the walls of the canisters may be tested against any number of propellants and drug formulations. In addition the effects of exposing the pMDIs to physical stresses, such as agitation, changes in temperature, etc. can also be studied. These tests can be performed over an extended period of time to determine potency decay rates by simply maintaining an inventory of stock pMDIs and performing tests at intervals of days, weeks or months.

As will be evident to those skilled in the arts of optical measurements and fluid dynamics and drug delivery and formulations, the benefits conveyed by the present invention are far reaching, and there are many obvious variations of the methods of the invention that do not depart from the fundamental elements that disclosed herein; all such variations are but obvious implementations of the described invention and are included by reference to our claims, which follow.

What is claimed is:

1. An apparatus comprising:
   an inlet valve;
   inlet tubing connecting the inlet valve to a measurement cell,
   wherein the inlet valve is located upstream of the measurement cell;
   an outlet valve,
   wherein the outlet valve is located downstream of the measurement cell;
   outlet tubing connecting the measurement cell to the outlet valve; and
   a rapid release adapter,
   wherein an outlet of the rapid release adapter is connected to an inlet port of the inlet valve,
   wherein an inlet port of the rapid release adapter is configured to be connected to a canister containing a liquid sample maintained in a liquid state by a pressure in the canister, and
   wherein the rapid release adapter is configured to release the liquid sample from the canister into the inlet valve and the inlet tubing, thereby releasing the liquid sample into the measurement cell; and
   wherein the measurement cell is configured to measure physical properties of the liquid sample in the measurement cell,
   wherein the liquid sample is maintained in a liquid state while the measurement cell measures the physical properties.

2. The apparatus of claim 1 wherein the measurement cell is an optical measurement cell.

3. The apparatus of claim 1 wherein the measurement cell is an element of an electrophoretic mobility detector.

4. The apparatus of claim 2 wherein the measurement cell is an element of a fluorescence detector.

5. The apparatus of claim 2 wherein the measurement cell is an element of a UV absorption detector.

6. The apparatus of claim 2 wherein the measurement cell is an element of a light scattering detector.

7. The apparatus of claim 6 wherein the light scattering detector is configured to measure dynamic light scattering.

8. The apparatus of claim 6 wherein the measurement cell is an element of a multiangle light scattering detector.

9. The apparatus of claim 3 wherein the electrophoretic mobility detector is an MP-PALS instrument.

10. The apparatus of claim 1 wherein the inlet valve is a check valve configured to permit the liquid sample to flow into the measurement cell and configured to prevent the liquid sample to flow away from the measurement cell.

11. The apparatus of claim 1 wherein the outlet valve comprises a first port connected to the measurement cell, and a second port connected to outlet flow tubing.

12. The apparatus of claim 1 wherein the outlet valve comprises a first port connected by tubing to the measurement cell, and a second port connected to a syringe configured to evacuate atmosphere contained within the measurement cell and dead volume between the inlet valve and the outlet valve.

13. The apparatus of claim 1 wherein the outlet valve is a three-way valve comprising a first port connected by tubing to the measurement cell, a second port connected to a waste line, and a third port connected to a syringe configured to evacuate atmosphere contained within the measurement cell and dead volume between the inlet valve and the outlet valve.

* * * * *